(12) United States Patent
Kwon et al.

(10) Patent No.: US 7,371,564 B2
(45) Date of Patent: May 13, 2008

(54) APPARATUS FOR AUTOMATICALLY ANALYZING GENETIC AND PROTEIN MATERIALS USING PHOTODIODES

(75) Inventors: Ho Taik Kwon, Seoul (KR); Jae Sik Park, Kunpo-Si (KR)

(73) Assignee: CELLTEK Co., Ltd., Seoul (KR)

(*) Notice: Subject to any disclaimer, the term of this patent is extended or adjusted under 35 U.S.C. 154(b) by 596 days.

(21) Appl. No.: 10/505,039

(22) PCT Filed: Feb. 27, 2002

(86) PCT No.: PCT/KR02/00322

§ 371 (c)(1),
(2), (4) Date: Aug. 18, 2004

(87) PCT Pub. No.: WO03/072825

PCT Pub. Date: Sep. 4, 2003

(65) Prior Publication Data

US 2005/0153294 A1    Jul. 14, 2005

(51) Int. Cl.
| | |
|---|---|
| C12M 1/34 | (2006.01) |
| C12Q 1/68 | (2006.01) |
| G01N 33/48 | (2006.01) |
| G01N 33/50 | (2006.01) |
| G01N 21/64 | (2006.01) |
| H04N 5/228 | (2006.01) |
| H03F 3/04 | (2006.01) |
| H01L 27/148 | (2006.01) |

(52) U.S. Cl. ............... 435/288.7; 435/287.2; 435/6; 435/20; 702/20; 250/461.2; 348/222.1; 330/250; 257/291

(58) Field of Classification Search ............ 435/288.7, 435/6, 287.2; 257/223, 292, 290; 702/20
See application file for complete search history.

(56) References Cited

U.S. PATENT DOCUMENTS 4,236,831 A * 12/1980 Hendrickson ............... 257/49

5,057,829 A * 10/1991 Velazquez .................. 370/465

(Continued)

FOREIGN PATENT DOCUMENTS

| IL | WO 01/69248 | * 9/2001 |
|---|---|---|
| JP | 407321368 | * 12/1995 |

OTHER PUBLICATIONS

JP407321368 Translation pp. 1-5.*

*Primary Examiner*—Walter D. Griffin
*Assistant Examiner*—Lydia Edwards
(74) *Attorney, Agent, or Firm*—Hoffmann & Baron, LLP

(57) ABSTRACT

An apparatus for automatically analyzing genetic and protein materials using photodiodes. The apparatus comprises a computer for controlling the entire operation of the apparatus and analyzing a voltage level from a characteristic detector to analyze states of the genetic and protein materials, and an address decoder connected to the computer. The photodiodes are connected to the address decoder and generate currents in response to external light being incident thereon. A plurality of amplifiers are connected respectively to the photodiodes to amplify output currents therefrom, and a plurality of voltage output circuits are connected respectively to the amplifiers to convert output currents therefrom into voltages. An output selector selects any one of output voltages from the voltage output circuits under the control of the computer. The characteristic detector measures a level of an output voltage from the output selector and applies the measured voltage level to the computer. A variety of genetic and protein materials corresponding to various diseases are attached to the photodiodes. If the external light is incident on the materials, then luminous fluxes vary depending on chemical structures of the materials, thereby causing the photodiodes to generate currents of amounts corresponding to the varying luminous fluxes, respectively.

8 Claims, 5 Drawing Sheets

U.S. PATENT DOCUMENTS

| | | | | |
|---|---|---|---|---|
| 5,436,171 A | * | 7/1995 | Kudo | 438/73 |
| 6,177,333 B1 | * | 1/2001 | Rhodes | 438/433 |
| 6,197,503 B1 | * | 3/2001 | Vo-Dinh et al. | 435/6 |
| 6,329,661 B1 | * | 12/2001 | Perov et al. | 250/461.2 |
| 6,369,426 B2 | * | 4/2002 | Blanchard et al. | 257/342 |
| 2001/0042875 A1 | * | 11/2001 | Yoshida | 257/291 |
| 2004/0027462 A1 | * | 2/2004 | Hing | 348/222.1 |

* cited by examiner

APPARATUS FOR AUTOMATICALLY ANALYZING GENETIC AND PROTEIN MATERIALS USING PHOTODIODES

CROSS-REFERENCE TO RELATED APPLICATION

This application is a National Phase application of International Application No. PCT/KR02/00322 filed Feb. 27, 2002, which is incorporated herein by reference.

BACKGROUND OF THE INVENTION

1. Field of the Invention

The present invention relates to an apparatus for automatically analyzing genetic and protein materials, and more particularly to an automatic genetic/protein material analyzer using photodiodes, wherein the photodiodes are adapted to generate currents of different amounts according to the amounts of light transmitted thereto, and a variety of protein materials and a variety of genetic materials such as DNA, RNA and the like are attached to the photodiodes and then applied with light so that they can be automatically analyzed on the basis of the amounts of currents flowing through the photodiodes.

2. Description of the Related Art

Recently, various diseases have developed with the advance of human civilization. For this reason, it is the current reality that human beings are faced with war with diseases. In order to rapidly detect and analyze various diseases, it is very effective to detect and analyze genetic materials or viruses causing such diseases. In this regard, for the purpose of rapidly and accurately analyzing and curing various diseases, it is necessary to accurately detect and analyze genetic materials or viruses causing such diseases. A conventional genetic material analyzer has been proposed to implant a genetic material onto a glass slide and then analyze a gene expression from the resultant fluorescence through the use of a laser fluorescence scanner so as to analyze disease states. However, the conventional genetic material analyzer has a disadvantage in that it is complicated in its construction and operation.

SUMMARY OF THE INVENTION

Therefore, the present invention has been made in view of the above problems, and it is an object of the present invention to provide an apparatus for automatically analyzing a variety of genetic and protein materials using photodiodes, wherein the genetic materials, such as DNA and the like, and the protein materials are attached on the upper surfaces of the photodiodes, which are formed on silicon substrates, and then applied with light so that they can be automatically analyzed by analyzing the amounts of currents which are generated from the photodiodes according to the amounts of light transmitted to the photodiodes through the genetic and protein materials.

In accordance with the present invention, the above and other objects can be accomplished by the provision of an apparatus for automatically analyzing genetic and protein materials using a plurality of photodiodes, comprising: a computer for controlling the entire operation of the apparatus and analyzing a voltage level from a characteristic detector to analyze states of the genetic and protein materials; an address decoder connected to the computer; the photodiodes being connected to the address decoder and generating currents in response to external light being incident thereon; a plurality of amplifiers connected respectively to the photodiodes for amplifying output currents therefrom; a plurality of voltage output circuits connected respectively to the amplifiers for converting output currents therefrom into voltages; an output selector connected in common to the voltage output circuits for selecting any one of output voltages therefrom under the control of the computer; and the characteristic detector connected to the output selector for measuring a level of an output voltage therefrom and applying the measured voltage level to the computer.

Preferably, the genetic and protein materials may be attached on a predetermined portion of each of the photodiodes and the apparatus may further comprise a light emitting device for emitting the external light simultaneously to the photodiodes, the external light being transmitted to the photodiodes through the genetic and protein materials.

The address decoder may include a row address decoder and a column address decoder, the photodiodes may be arranged at a desired region and connected in common to the row address decoder and column address decoder, and the apparatus may further comprise a light emitting device installed adjacent to the desired region for emitting the external light simultaneously to the photodiodes.

Each of the photodiodes may include: a silicon substrate; an n-type silicon layer formed on the silicon substrate, the n-type silicon layer being an epitaxial layer; a p+ region formed in one portion of the n-type silicon layer through a diffusion process; an n+ region formed in another portion of the n-type silicon layer at a certain distance from the p+ region; a first silicon oxide film formed over the n-type silicon layer, p+ region and n+ region; a pair of holes formed through the first silicon oxide film; a pair of electrodes formed respectively in the holes in such a manner that they come into contact with the p+ region and n+ region; a second silicon oxide film formed over the electrodes and first silicon oxide film; a barrier film formed on the second silicon oxide film; a third silicon oxide film formed on the barrier film; a buried region formed by etching the first to third silicon oxide films and the barrier film to a certain thickness of the first silicon oxide film between the p+ region and the n+ region; and a silicon nitride film formed on a portion of the first silicon oxide film, corresponding to a bottom surface of the buried region.

The genetic and protein materials may be positioned on the silicon nitride film of the bottom surface of the buried region in each of the photodiodes, and the apparatus may further comprise a light emitting device installed over the genetic and protein materials for emitting the external light simultaneously to the photodiodes, the external light being transmitted to the photodiodes through the genetic and protein materials.

The apparatus may further comprise a photodiode interface connected between the column address decoder and the photodiodes, the photodiode interface including a plurality of first switching transistors having their base terminals connected to the column address decoder and their collector terminals connected respectively to the photodiodes, and a plurality of current limit resistors connected respectively to the photodiodes, each of the amplifiers being connected to a corresponding one of the photodiodes via a corresponding one of the current limit resistors.

The apparatus may further comprise a plurality of preamplifiers connected respectively between the photodiodes and the amplifiers for preamplifying the output currents from the photodiodes to improve current amplification factors of the amplifiers, each of the preamplifiers including a first current amplification transistor having its collector terminal connected to a corresponding one of the photodiodes via a corresponding one of the current limit resistors, a second current amplification transistor having its base terminal connected to a base terminal of the first current amplification transistor and its collector terminal connected to a corresponding one of the amplifiers, and a third current amplification transistor having its base terminal connected in common to the collector terminal of the first current amplification transistor and to the corresponding photodiode via the corresponding current limit resistor and its emitter terminal connected in common to the base terminals of the first and second current amplification transistors.

Each of the amplifiers may include a second switching transistor having its base terminal connected to the row address decoder and its collector terminal connected to the collector terminal of the second current amplification transistor, a fourth current amplification transistor having its base terminal and collector terminal connected in common to the collector terminal of the second current amplification transistor and the collector terminal of the second switching transistor, and a fifth current amplification transistor having its base terminal connected in common to the base and collector terminals of the fourth current amplification transistor, the collector terminal of the second current amplification transistor and the collector terminal of the second switching transistor, each of the current amplification factors of the amplifiers being determined based on a ratio of amplification degrees of the fourth and fifth current amplification transistors, each of the output currents from the photodiodes being amplified by the first to third current amplification transistors and the fourth and fifth current amplification transistors, converted into a voltage through a load and then applied to the output selector.

In a feature of the present invention, a plurality of photodiodes are connected to an address decoder, which is in turn connected to a computer. The address decoder is provided with a row address decoder and a column address decoder. First switching transistors in a photodiode interface are connected respectively between the photodiodes and the column address decoder to select corresponding ones of the photodiodes under control of the column address decoder. First to third current amplification transistors are connected to a corresponding one of the photodiodes via the photodiode interface to primarily amplify output current from the corresponding photodiode. Fourth and fifth current amplification transistors are connected to the row address decoder and secondarily amplify the output current from the corresponding photodiode. A current limit resistor is connected between the first to third current amplification transistors and the corresponding photodiode to prevent an interference between the corresponding photodiode and the adjacent photodiode. The current limit resistor also acts to limit the amount of current flowing through the corresponding photodiode so as to prevent a large amount of current from suddenly flowing through the corresponding photodiode. A variety of genetic and protein materials corresponding to various diseases are attached to the photodiodes. If light is incident on the genetic and protein materials, then luminous fluxes vary depending on chemical structures of the materials, thereby causing the photodiodes to generate currents of amounts corresponding to the varying luminous fluxes, respectively. Output current from each of the photodiodes is amplified by an amplifier, converted into a voltage by a voltage output circuit, selected by an output selector and then applied to a characteristic detector. The characteristic detector measures the level of an output voltage from the voltage output circuit and applies the measured voltage level to the computer. The computer performs a comparison/analysis operation for the voltage level applied from the characteristic detector and diagnoses disease states as a result of the comparisin/analysis operation.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
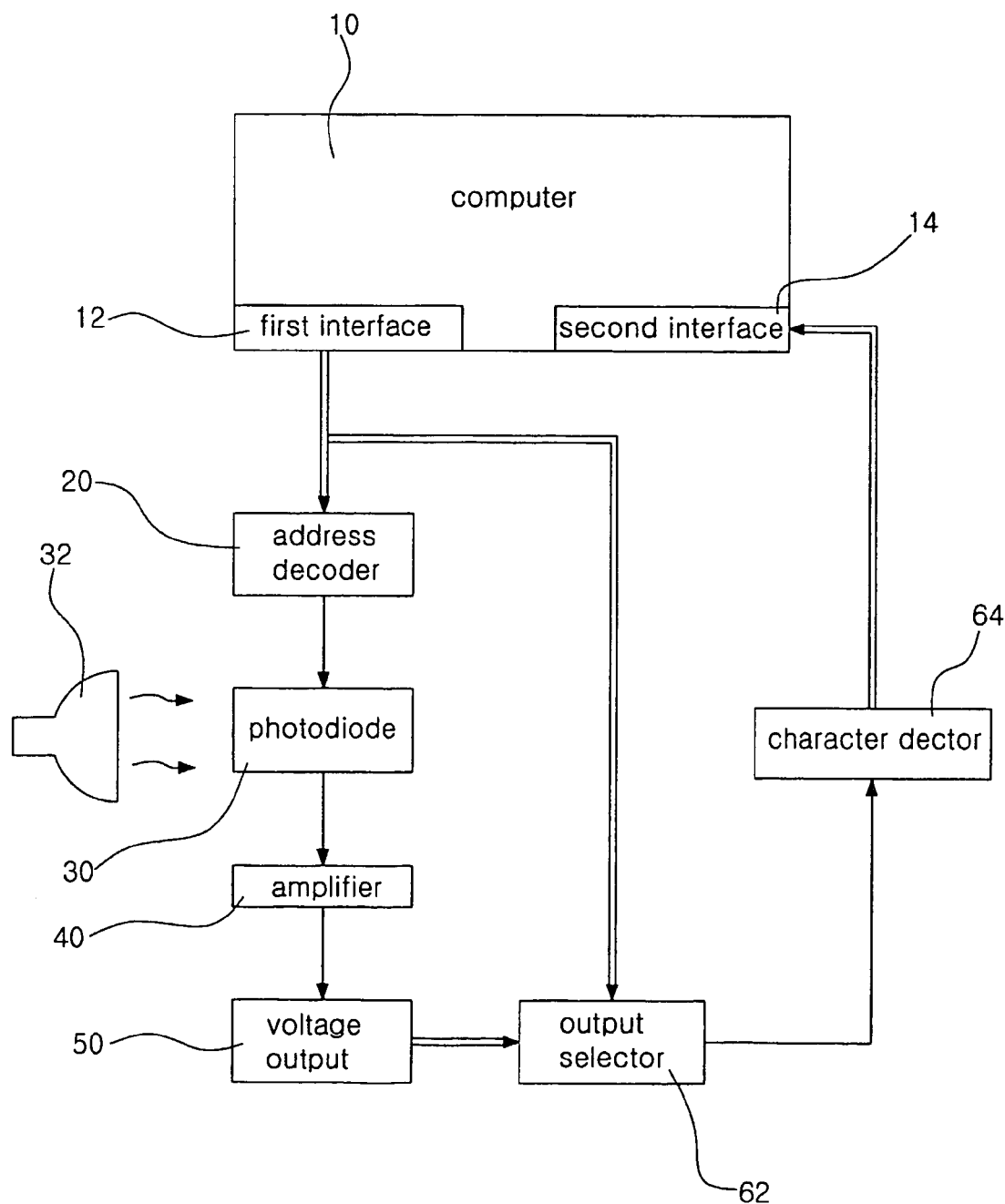
FIG. 1 is a block diagram schematically showing the construction of an apparatus for automatically analyzing genetic and protein materials using photodiodes in accordance with the present invention.
Figure 2:
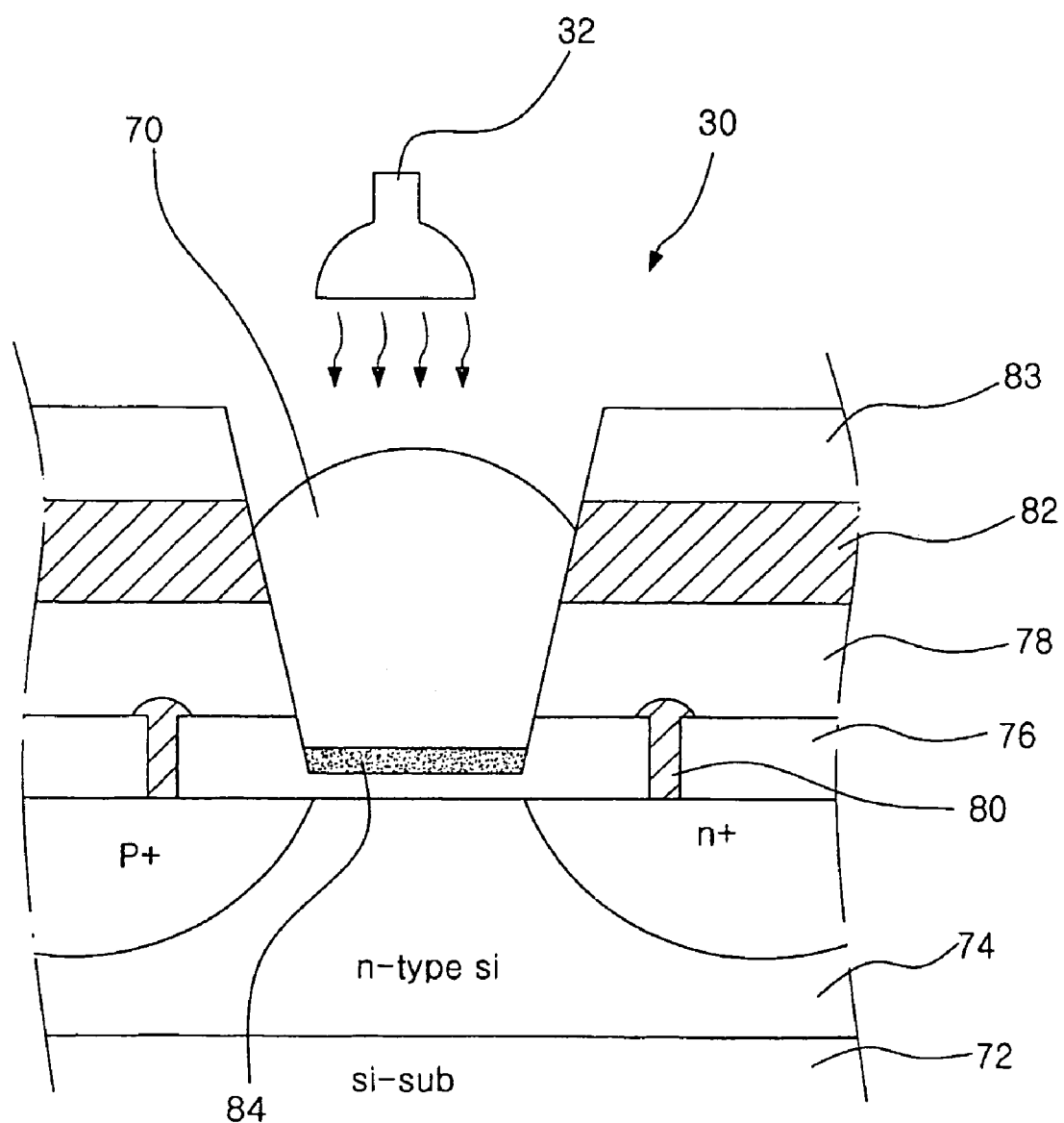
FIG. 2 is a schematic sectional view of the photodiodes used in the automatic genetic/protein material analyzer in accordance with the present invention.
Figure 3:
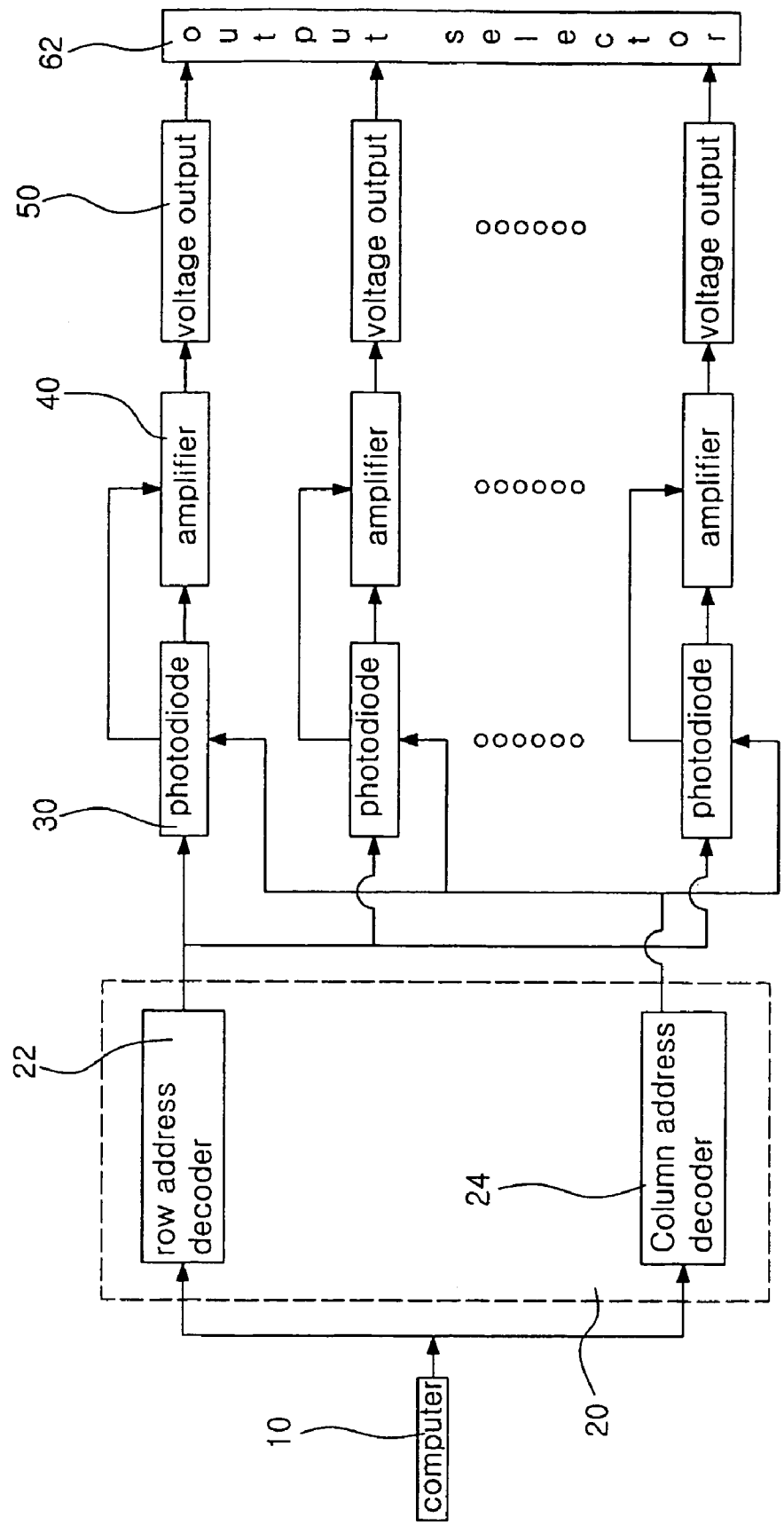
FIG. 3 is a detailed block diagram of the automatic genetic/protein material analyzer in accordance with the present invention.
Figure 4:
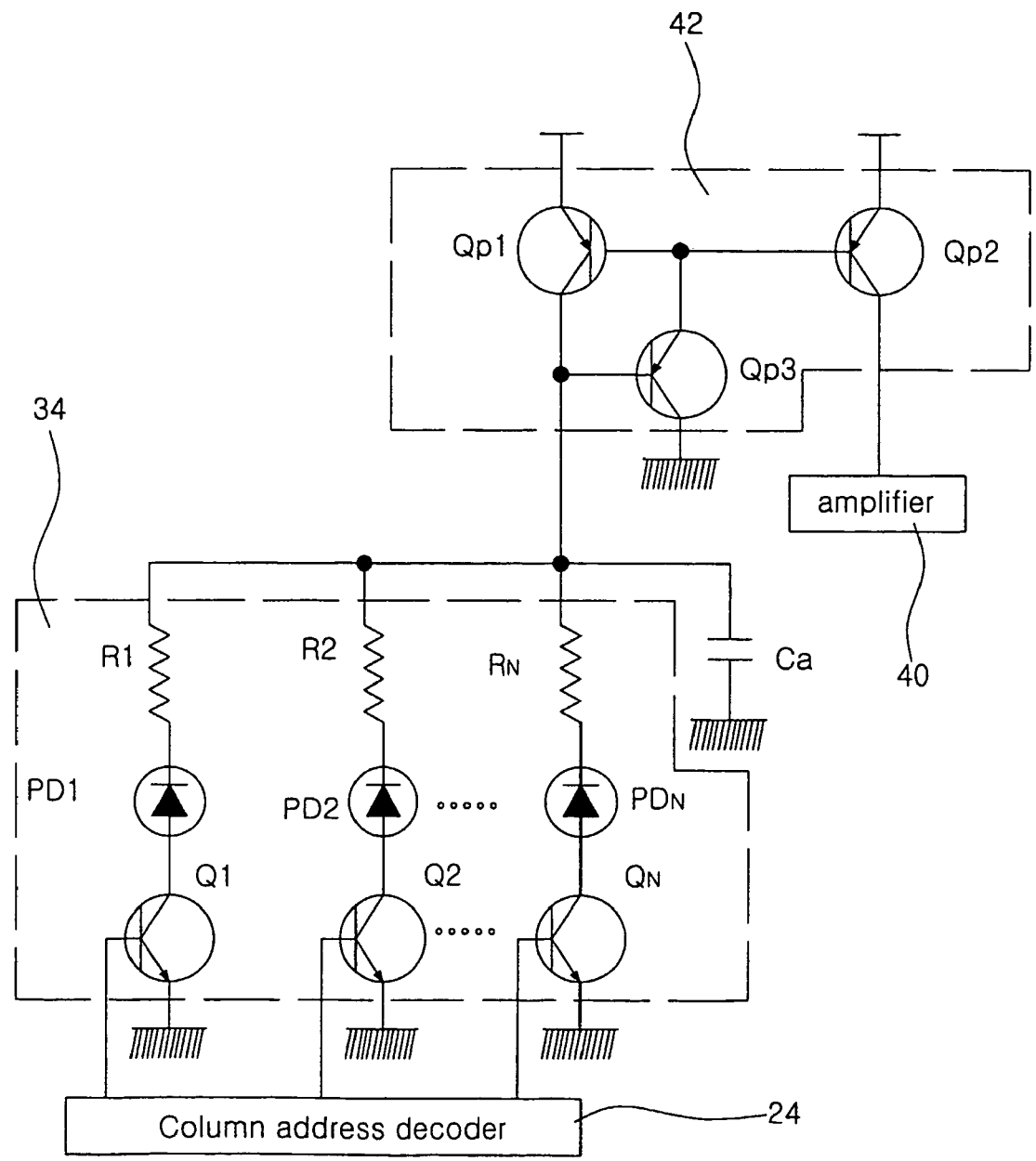
FIG. 4 is a circuit diagram of a photodiode interface connected to a column address decoder of the automatic genetic/protein material analyzer in accordance with the present invention.
Figure 5:
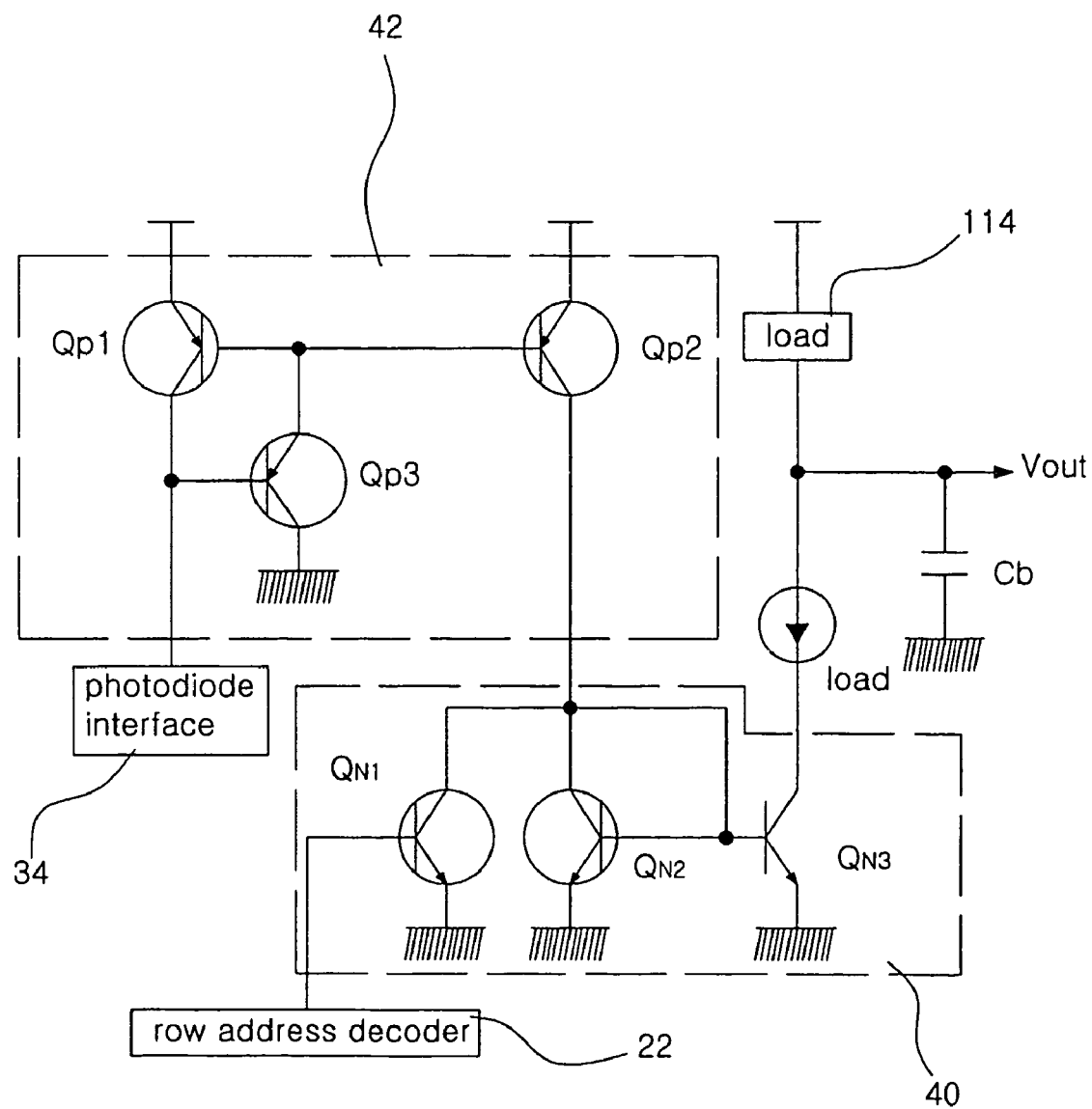
FIG. 5 is a circuit diagram of a current amplification circuit connected to a row address decoder of the automatic genetic/protein material analyzer in accordance with the present invention.

FIG. 1 is a block diagram schematically showing the construction of an apparatus for automatically analyzing genetic and protein materials using photodiodes in accordance with the present invention, FIG. 2 is a schematic sectional view of the photodiodes used in the automatic genetic/protein material analyzer in accordance with the present invention, FIG. 3 is a detailed block diagram of the automatic genetic/protein material analyzer in accordance with the present invention, FIG. 4 is a circuit diagram of a photodiode interface connected to a column address decoder of the automatic genetic/protein material analyzer in accordance with the present invention, and FIG. 5 is a circuit diagram of a current amplification circuit connected to a row address decoder of the automatic genetic/protein material analyzer in accordance with the present invention.

A preferred embodiment of the present invention will hereinafter be described with reference to FIGS. 1 to 5.

As shown, a computer 10 is provided to control the entire operation of the automatic genetic/protein material analyzer using the photodiodes in accordance with the present invention. An address decoder 20 is connected to the computer 10 via a first interface 12. The address decoder 20 is provided with a row address decoder 22 and a column address decoder 24. A plurality of photodiodes 30 are connected to the address decoder 20. The photodiodes 30 are arranged at a desired region (not shown). A light emitting device 32 is installed adjacent to the photodiode region. The light emitting device 32 emits light simultaneously to the photodiodes 30 arranged at the desired region.

A genetic material, such as DNA, RNA or the like, and a protein material are attached to each of the photodiodes 30. If the light emitted from the light emitting device 32 is incident on the genetic and protein materials of the photodiodes 30, then luminous fluxes to be applied to the photodiodes 30 through the genetic and protein materials vary depending on chemical structures of the genetic and protein materials, thereby causing the photodiodes 30 to generate currents of amounts corresponding to the varying luminous fluxes, respectively. An amplifier 40 is connected to each of the photodiodes 30. The amplifier 40 amplifies current generated and applied from a corresponding one of the photodiodes 30. A voltage output circuit 50 is connected to the amplifier 40. The voltage output circuit 50 converts output current from the amplifier 40 into a voltage and feeds the resulting voltage to an output selector 62. The amplifier 40 and voltage output circuit 50 are connected to each of the photodiodes 30, and the output selector 62 is connected in common to the respective voltage output circuits 50. The output selector 62 selects any one of the voltage output circuits 50 under the control of the computer 10 and transfers an output voltage from the selected voltage output circuit 50 to a characteristic detector 64. The characteristic detector 64 measures the level of the output voltage from the voltage output circuit 50 selected by the output selector 62 and applies the measured voltage level to the computer 10 via a second interface 14. The computer 10 performs a comparison/analysis operation for the voltage level applied from the characteristic detector 64 and analyzes characteristics of the genetic and protein materials attached to the photodiode 30 connected to the voltage output circuit 50 selected by the output selector 62, as a result of the comparison/analysis operation.

Each of the photodiodes 30 includes a silicon substrate 72, and an epitaxial layer, or n-type silicon layer 74, formed on the silicon substrate 72. The n-type silicon layer 74 is then subjected to a diffusion process such that a p+ region is formed in one portion thereof and an n+ region is formed in another portion thereof at a certain distance from the p+ region. A first silicon oxide film 76 is formed over the n-type silicon layer 74, p+ region and n+ region. Holes are formed through the first silicon oxide film 76 and electrodes 80 are then formed respectively in the holes to come into contact with the p+ region and n+ region. A second silicon oxide film 78 is formed over the electrodes 80 and first silicon oxide film 76. A barrier film 82 is formed on the second silicon oxide film 78 and a third silicon oxide film 83 is then formed on the barrier film 82. The electrodes 80 and barrier film 82 are made of metal materials, and the barrier film 82 blocks portions other than a desired portion of the second silicon oxide film 78 to direct the light from the light emitting device 32 to only the desired portion.

The first to third silicon oxide films 76, 78 and 83 and the barrier film 82 are then etched to a certain thickness of the first silicon oxide film 76 between the p+ region and the n+ region to form a buried region. A silicon nitride film 84 is formed on a portion of the first silicon oxide film 76, corresponding to the bottom surface of the buried region. A genetic material and protein material 70 to be analyzed are then positioned on the silicon nitride film 84 of the bottom surface of the buried region. The silicon nitride film 84 acts to increase adhesion of the genetic and protein materials 70 to the photodiode.

After the genetic and protein materials 70 are positioned in the buried region of the photodiode 30 with the above-described structure, the light emitted from the light emitting device 32 is projected onto the genetic and protein materials 70. If the light from the light emitting device 32 is projected onto the genetic and protein materials 70, then it is passed through the materials 70 and applied to the n-type silicon layer 74 of the photodiode 30, resulting in current flowing through the silicon layer 74. At this time, the amount of current flowing through the n-type silicon layer 74 is in proportion to the amount of light applied to the silicon layer 74. The amount of light applied to the n-type silicon layer 74 through the genetic and protein materials 70 depends on chemical structures of the materials 70. Alternatively, a specific material reacting with the genetic and protein materials 70, such as blood plasma, may be implanted into the materials 70. In this case, the amount of light applied to the n-type silicon layer 74 through the genetic and protein materials 70 varies with the reaction of the specific material to the materials 70. As a result, it can be recognized whether the specific material reacts with the genetic and protein materials 70.

In other words, because the amount of current flowing through the n-type silicon layer 74 is different according to the genetic and protein materials 70, characteristics of the materials 70 and disease states can be analyzed by measuring the amount of current flowing through the silicon layer 74. The amplifier 40 amplifies current generated from the photodiode 30 because it is weak in level. Output current from the amplifier 40 is converted into a voltage by the voltage output circuit 50 and then supplied to the characteristic detector 64.

The characteristic detector 64 measures the level of an output voltage from the voltage output circuit 50 and applies the measured voltage level to the computer 10 via the second interface 14. The computer 10 performs the comparison/analysis operation for the voltage level applied from the characteristic detector 64 and analyzes the states of the genetic and protein materials 70 as a result of the comparison/analysis operation. On the basis of the analysis results, the computer 10 can diagnose characteristics of the genetic and protein materials 70 and disease states.

A photodiode interface 34 is connected between the column address decoder 24 and the photodiodes 30 PD1-PDN. The photodiode interface 34 includes a plurality of first switching transistors Q1-QN having their base terminals connected to the column address decoder 24 and their collector terminals connected respectively to the photodiodes PD1-PDN. The photodiode interface 34 further includes a plurality of current limit resistors R1-RN connected respectively to the photodiodes PD1-PDN, and a noise removal capacitor Ca connected in common to the current limit resistors R1-RN. The amplifier 40 is connected to a corresponding one of the photodiodes PD1-PDN via a corresponding one of the current limit resistors R1-RN.

A preamplifier 42 is connected between a corresponding one of the photodiodes PD1-PDN and the amplifier 40 to preamplify current generated from the corresponding photodiode so as to improve a current amplification factor of the amplifier 40. The preamplifier 42 includes a first current amplification transistor Qp1 having its collector terminal connected to the corresponding photodiode via a corresponding one of the current limit resistors R1-RN, a second current amplification transistor Qp2 having its base terminal connected to a base terminal of the first current amplification transistor Qp1 and its collector terminal connected to the amplifier 40, and a third current amplification transistor Qp3 having its base terminal connected in common to the collector terminal of the first current amplification transistor Qp1 and to the corresponding photodiode via the corresponding current limit resistor and its emitter terminal connected in common to the base terminals of the first and second current amplification transistors Qp1 and Qp2.

The amplifier 40 constitutes a current amplification circuit together with the preamplifier 42. The amplifier 40 includes a second switching transistor QN1 having its base terminal connected to the row address decoder 22 and its collector terminal connected to the collector terminal of the second current amplification transistor Qp2, a fourth current amplification transistor QN2 having its base terminal and collector terminal connected in common to the collector terminal of the second current amplification transistor Qp2 and the collector terminal of the second switching transistor QN1, and a fifth current amplification transistor QN3 having its base terminal connected in common to the base and collector terminals of the fourth current amplification transistor QN2, the collector terminal of the second current amplification transistor Qp2 and the collector terminal of the second switching transistor QN1. The current amplification factor of the amplifier 40 is determined based on a ratio of amplification degrees of the fourth and fifth current amplification transistors QN2 and QN3. Output current Iout amplified by the first to third current amplification transistors Qp1-Qp3 and the fourth and fifth current amplification transistors QN2 and QN3 is converted into a voltage through a load and then applied to the output selector. A capacitor Cb acts to remove noise from the output voltage.

As apparent from the above description, according to the present invention, genetic and protein materials are positioned in a buried region of a photodiode and applied with light from a light emitting device. The applied light is transmitted to an n-type silicon layer of the photodiode through the genetic and protein materials. The amount of current generated from the photodiode varies with the amount of light transmitted to the n-type silicon layer. Namely, the amount of current flowing through the photodiode is different according to the amount of light transmitted to the n-type silicon layer. In this connection, a computer performs a comparison/analysis operation for a voltage level from a characteristic detector, corresponding to the amount of current flowing through the photodiode, and accurately analyzes the states of the genetic and protein materials as a result of the comparison/analysis operation. On the basis of the analysis results, the computer can diagnose characteristics of the genetic and protein materials and disease states.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for automatically analyzing genetic and protein materials using a plurality of photodiodes, comprising:
   a computer for controlling the entire operation of the apparatus and analyzing a voltage level from a characteristic detector to analyze states of the genetic and protein materials;
   an address decoder connected to said computer;
   said photodiodes being connected to said address decoder and generating currents in response to external light being incident thereon;
   a plurality of amplifiers for amplifying output currents from the photodiodes, each of the plurality of photodiodes being directly connected to a different one of the plurality of amplifiers, each of the plurality of amplifiers being directly connected to a different one of the plurality of photodiodes;
   a plurality of voltage output circuits for converting output currents from the plurality of amplifiers into voltages, each of the plurality of amplifiers being directly connected to a different one of the plurality of voltage output circuits, each of the plurality of voltage output circuits being directly connected to a different one of the plurality of amplifiers;
   an output selector connected in common to said voltage output circuits for selecting any one of output voltages therefrom under the control of said computer; and
   said characteristic detector connected to said output selector for measuring a level of an output voltage therefrom and applying the measured voltage level to said computer.

2. The apparatus as set forth in claim 1, wherein said genetic and protein materials are attached on a predetermined portion of each of said photodiodes and wherein the apparatus further comprises a light emitting device for emitting said external light simultaneously to said photodiodes, said external light being transmitted to said photodiodes through said genetic and protein materials.

3. The apparatus as set forth in claim 1, wherein said address decoder includes a row address decoder and a column address decoder, wherein said photodiodes are arranged at a desired region and connected in common to said row address decoder and column address decoder, and wherein the apparatus further comprises a light emitting device installed adjacent to said desired region for emitting said external light simultaneously to said photodiodes.

4. The apparatus as set forth in claim 3, further comprising a photodiode interface connected between said column address decoder and said photodiodes, said photodiode interface including a plurality of first switching transistors having their base terminals connected to said column address decoder and their collector terminals connected respectively to said photodiodes, and a plurality of current limit resistors connected respectively to said photodiodes, each of said amplifiers being connected to a corresponding one of said photodiodes via a corresponding one of said current limit resistors.

5. The apparatus as set forth in claim 4, further comprising a plurality of preamplifiers connected respectively between said photodiodes and said amplifiers for preamplifying the output currents from said photodiodes to improve current amplification factors of said amplifiers, each of said preamplifiers including a first current amplification transistor having its collector terminal connected to a corresponding one of said photodiodes via a corresponding one of said current limit resistors, a second current amplification transistor having its base terminal connected to a base terminal of said first current amplification transistor and its collector terminal connected to a corresponding one of said amplifiers, and a third current amplification transistor having its base terminal connected in common to said collector terminal of said first current amplification transistor and to said corresponding photodiode via said corresponding current limit resistor and its emitter terminal connected in common to said base terminals of said first and second current amplification transistors.

6. The apparatus as set forth in claim 5, wherein each of said amplifiers includes a second switching transistor having its base terminal connected to said row address decoder and its collector terminal connected to said collector terminal of said second current amplification transistor, a fourth current amplification transistor having its base terminal and collector terminal connected in common to said collector terminal of said second current amplification transistor and said collector terminal of said second switching transistor, and a fifth current amplification transistor having its base terminal connected in common to said base and collector terminals of said fourth current amplification transistor, said collector terminal of said second current amplification transistor and said collector terminal of said second switching transistor, each of said current amplification factors of said amplifiers being determined based on a ratio of amplification degrees of said fourth and fifth current amplification transistors, each of said output currents from said photodiodes being amplified by said first to third current amplification transistors and said fourth and fifth current amplification transistors, converted into a voltage through a load and then applied to said output selector.

7. The apparatus as set forth in claim 1, wherein each of said photodiodes includes: a silicon substrate; an n-type silicon layer formed on said silicon substrate, said n-type silicon layer being an epitaxial layer; a p+ region formed in one portion of said n-type silicon layer through a diffusion process; an n+ region formed in another portion of said n-type silicon layer at a certain distance from said p+ region; a first silicon oxide film formed over said n-type silicon layer, p+ region and n+ region; a pair of holes formed through said first silicon oxide film; a pair of electrodes formed respectively in said holes in such a manner that they come into contact with said p+ region and n+ region; a second silicon oxide film formed over said electrodes and first silicon oxide film; a barrier film formed on said second silicon oxide film; a third silicon oxide film formed on said barrier film; a buried region formed by etching said first to third silicon oxide films and said barrier film to a certain thickness of said first silicon oxide film between said p+ region and said n+ region; and a silicon nitride film formed on a portion of said first silicon oxide film, corresponding to a bottom surface of said buried region.

8. The apparatus as set forth in claim 7, wherein said genetic and protein materials are positioned on said silicon nitride film of said bottom surface of said buried region in each of said photodiodes and wherein the apparatus further comprises a light emitting device installed over said genetic and protein materials for emitting said external light simultaneously to said photodiodes, said external light being transmitted to said photodiodes through said genetic and protein materials.

* * * * *